United States Patent

Springer

Patent Number: 5,811,454
Date of Patent: Sep. 22, 1998

[54] 4-AMINO-FLUOROBENZAMIDES AND THEIR USE AS CYTOTOXIC PRODRUGS

[75] Inventor: Caroline J. Springer, Sutton, United Kingdom

[73] Assignee: Cancer Research Campaign Technology Limited, London, United Kingdom

[21] Appl. No.: 537,890
[22] PCT Filed: May 3, 1994
[86] PCT No.: PCT/GB94/00941
   § 371 Date: Dec. 21, 1995
   § 102(e) Date: Dec. 21, 1995
[87] PCT Pub. No.: WO94/25429
   PCT Pub. Date: Nov. 10, 1994

[30] Foreign Application Priority Data

Apr. 30, 1993 [GB] United Kingdom .................. 9308957

[51] Int. Cl.[6] .................. A61K 31/235; C07C 229/14
[52] U.S. Cl. .................. 514/517; 514/533; 558/47; 558/48; 562/565
[58] Field of Search .................. 562/565; 558/47, 558/48; 514/517, 533

[56] References Cited

FOREIGN PATENT DOCUMENTS

88/07378  10/1988  WIPO .

OTHER PUBLICATIONS

Springer, Caroline J., "Novel Prodrugs Which are Activated to Cytotoxic Alkylating Agents by Carboxypeptidase G2", J. Med. Chem. 33:677–681, 1990.

*Primary Examiner*—Johann Richter
*Assistant Examiner*—Taofiq A. Solola
*Attorney, Agent, or Firm*—Spencer & Frank

[57] ABSTRACT

The invention provides a compound which is a 3-fluorobenzamide of the formula (A)

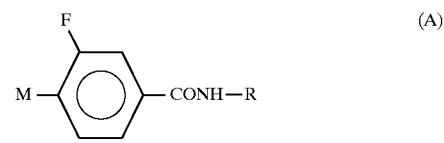

wherein R-NH is the residue of an α-amino acid R-NH$_2$ or oligopeptide R-NH$_2$, and M is a nitrogen mustard group of the formula

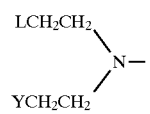

wherein Y and L, which may be the same or different in a molecule, are leaving groups; or a pharmaceutically acceptable salt thereof. The compounds are useful as prodrugs for treating cancer.

13 Claims, No Drawings

4-AMINO-FLUOROBENZAMIDES AND THEIR USE AS CYTOTOXIC PRODRUGS

CROSS REFERENCE TO RELATED APPLICATIONS

This application is filed under 35 U.S.C. §371(c) as a continuation of International Application PCT/GB94/00941, filed May 3, 1994, which is based on U.K. Application No. 9308957.1, filed on Apr. 30, 1993 the priority of which is claimed.

This invention relates to prodrugs, their use in therapy and a process for their preparation.

TECHNOLOGY REVIEW

Over the years, many cytotoxic compounds have been discovered which are of potential use in cancer chemotherapy. Nitrogen mustards from one important family of such cytotoxic compounds. The clinical use of cytotoxic compounds in general and nitrogen mustards in particular has been limited because of the poor selectivity in the cytotoxic effect between tumour cells and normal cells.

One approach to overcome this problem has involved the development of so-called prodrugs which are derivatives of the cytotoxic drug, often a relatively simple derivative, whose cytotoxic properties are considerably reduced compared to those of the parent drug. Numerous proposals have been made for the administration of such prodrugs to patients under regimes whereby the prodrug is only converted to the cytotoxic drug in the region of the intended site of action.

SUMMARY OF THE INVENTION

One particularly promising approach involves the conversion of the nitrogen mustard into a reaction product with an amino acid or oligopeptide to form a prodrug which can be converted to the parent nitrogen mustard at the site of intended action under the influence of an enzyme. This approach can be put into practice by the utilization of an antibody/enzyme conjugate in association with a prodrug. The antibody/enzyme conjugate is one formed from an antibody to a tumour-associated antigen and an enzyme that will convert the prodrug to the cytotoxic drug. In clinical practice, the antibody/enzyme conjugate is first administered to the patient and is allowed to localise in the region of the tumour to be treated. The prodrug is then administered to the patient so that conversion of the prodrug to the cytotoxic drug is also localised in the region of the tumour to be treated under the influence of the localised enzyme. Such a system is described in our WO-A-88/07378, and is now called "antibody-directed enzyme prodrug therapy" (ADEPT).

Specific prodrugs that can be used in ADEPT are those based upon benzoic acid nitrogen mustards (WO-A-88/07378). The cytotoxic benzoic acid nitrogen mustard is a bifunctional alkylating agent and the activating effect of the ionised carboxyl group is masked in the prodrug by converting the carboxyl group into an amide by reaction with an α-amino acid, the preferred α-amino acid being glutamic acid. The relatively inactive prodrug can be activated to its corresponding benzoic acid at a tumour site by prior administration of a monoclonal antibody coupled to the enzyme carboxypeptidase G2 (CPG2). Benzoic acid nitrogen mustard prodrugs and their cytotoxic drugs are also described in Springer et al., J. Med. Chem., (1990) 33, 677–681 and Springer et al., Anti-Cancer Drug Design (1991) 6, 467–479.

It is desirable to release a very reactive drug at the tumour in ADEPT. It is therefore an advantage to have prodrugs and corresponding active drugs of high reactivities, so that high efficacy in vivo may be obtained.

DETAILED DESCRIPTION OF THE INVENTION

I have now synthesized 2- and 3-fluoro ring substituted benzoic acid nitrogen mustards of general formula (A')

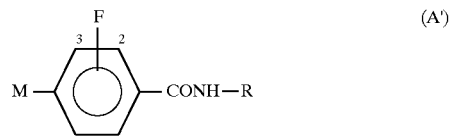

wherein R-NH is the residue of an α-amino acid R-NH$_2$ or oligopeptide R-NH$_2$, and M is a nitrogen mustard group of the formula

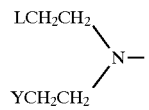

wherein Y and L, which may be the same or different in a molecule, are leaving groups; and pharmaceutically acceptable salts thereof. The F group may be at the 2- or 3-position relative to the —CONH-R group.

I have found that these compounds have surprising reactivities. Due to the strong inductive effect of fluorine, it would have been expected that a fluorine in the ring at position 2 or 3 would cause deactivation of the alkylating moiety, and that the inductive effect would be greater in the 3-position than in the 2-position. Thus, theoretically this would lead to the 3-fluoro compounds being less reactive than the 2-fluoro compounds. However, I found that although the 2-fluoro prodrugs and their corresponding drugs are deactivated as expected (i.e. less reactive than their non-fluorinated analogues), the 3-fluoro prodrugs and drugs are greatly activated (i.e. much more reactive than their non-fluorinated analogues). Further, all of the 3-fluoro but not all of the 2-fluoro prodrugs tested are good substrates for CPG 2.

WO 93/08288 discloses 2- and 3-fluoro ring substituted nitrogen mustard compounds, but these compounds contain an —NH$_2$ group in place of the protected carboxyl group of the present benzoic acid nitrogen mustard based prodrugs. The compounds containing an —NH$_2$ group are very reactive and the addition of a 3-fluoro group makes no significant difference to their reactivity, in contrast to the great increase in reactivity caused by the 3-fluoro group in the present compounds.

The present invention provides a compound which is a 3-fluorobenzamide of the formula (A)

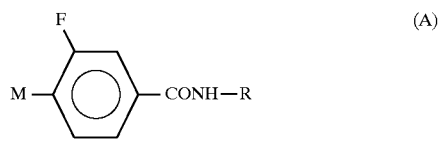

wherein R-NH is the residue of an α-amino acid R-NH$_2$ or oligopeptide R-NH$_2$, and M is a nitrogen mustard group of the formula

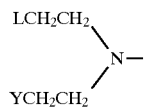

wherein Y and L, which may be the same or different in a molecule, are leaving groups; or a pharmaceutically acceptable salt thereof.

The prodrug is converted into the active drug by cleavage of the amide bond between the residue of the α-amino acid R-NH$_2$ or oligopeptide R-NH$_2$ and the residue of the benzoic acid nitrogen mustard. The active drug has the formula (B)

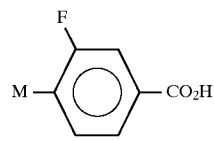

wherein M is as defined above.

The prodrug is suitable for use in a method of treatment of the human or animal body by therapy, particularly a method of treatment of cancer. The invention includes a method of treating a human or animal suffering from cancer, which method comprises administering to the patient a prodrug of the invention. The cancer may be any disease in which there is neoplastic cell growth, including leukemias and solid tumours (e.g. colorectal and ovarian tumours).

The prodrug may be selectively converted to the active drug by the enzyme component of an immunoglobulin/enzyme conjugate localised in the region of a tumour to be treated. Accordingly, the prodrug may be used in a method which comprises administering to a human or animal suffering from cancer pharmaceutically effective amounts of (i) an immunoglobulin/enzyme conjugate in which the immunoglobulin is specific for a tumour-associated antigen, and the enzyme will cleave the amide bond between the residue of the α-amino acid R-NH$_2$ or oligopeptide R-NH$_2$ and the benzoic acid nitrogen mustard residue; and thereafter (ii) the said prodrug.

Examples of suitable immunoglobulins and enzymes are given in WO-A-88/07378. The immunoglobulin may be an antibody or a fragment of an antibody containing at least one of the antigen binding sites of the antibody. The antibody is preferably monoclonal but could be polyclonal. The antibody will generally be of the IgG class but other classes of antibody are not excluded. The antibody may be humanised, e.g. as described by Winter in EP-A-239 400. The antibody fragment is generally a Fab' or F(ab')$_2$ fragment. The enzyme is preferably a carboxypeptidase (e.g. bacterial carboxypeptidase G2 (CPG2)).

In the prodrug of the invention, the groups Y and L, which may be the same or different in a molecule, may for example be halo, mesyloxy or 4-tosyloxy. Preferably, Y and L are both mesyloxy, Y and L are both chloro, or Y is mesyloxy and L is chloro.

The amino acid or oligopeptide R-NH$_2$ is selected in order that the group R-NH of prodrugs of the invention may be removed in vivo under the influence of an enzyme. Glutamic acid and aspartic acid are suitable amino acids, although other α-amino carboxylic acids may also be of use. The amino acids are preferably in the L configuration.

Examples of prodrugs of the invention are 3-fluoro-4-[bis-[2-(mesyloxy)ethyl]amino]benzoyl-L-glutamic acid, 3-fluoro-4-[(2-chloroethyl)[2-(mesyloxy)ethyl]amino]benzoyl-L-glutamic acid, 3-fluoro-4-[bis(2-chloroethyl)amino]benzoyl-L-glutamic acid, and pharmaceutically acceptable salts thereof.

The prodrugs of the invention may be produced by processes analogous to those described in WO-A-88/07378, WO-A-90/02729 and WO-A-91/03460.

The process of the present invention comprises deprotecting a compound of the formula (C)

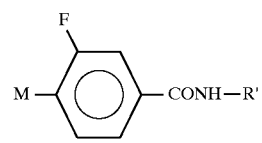

wherein M is as defined above, and R'-NH is the residue of an α-amino acid R'-NH$_2$ or oligopeptide R'-NH$_2$ containing at least one protected carboxylic acid group, and optionally converting the resulting compound of formula (A) as defined above into a pharmaceutically acceptable salt thereof. The compound of formula (C) is novel and forms part of the invention.

The at least one protected carboxylic acid group may, for example, be protected by an ethyl or tertiary butyl group. WO-A-88/07378 describes conventional methods of removing ethyl protecting groups which may be used in the present invention. In these methods, the ethyl protecting groups are removed by alkaline hydrolysis with aqueous sodium hydroxide followed by conversion of the resulting sodium salt into the free carboxylic acid using hydrochloric acid.

Preferably, the protecting groups are tertiary butyl. WO-A-90/02729 describes a suitable method of removing the tertiary butyl protecting groups. The tertiary butyl ester groups can be converted into free carboxylic acid groups by treatment with an acid, for example in a non-aqueous medium. Trifluoroacetic acid and formic acid are suitable acids. Removal of the tertiary butyl ester group can be carried out quite simply by maintaining the tertiary butyl ester in a substantially non-aqueous solution together with trifluoroacetic acid at room temperature, e.g. 15°–25° C. It is desirable to utilise an amount of trifluoroacetic acid that is at least equivalent to the tertiary butyl ester groups to be hydrolysed although the exact proportion of trifluoroacetic acid and the hydrolysis temperature are not critical, the use of lower temperatures and smaller proportions of trifluoroacetic acid serving merely to prolong the period of time necessary for total hydrolysis of the tertiary butyl ester groups to take place. Hydrolysis of tertiary butyl ester groups with trifluoroacetic acid under non-aqueous conditions proceeds almost quantitatively (>80%).

The compound of formula (C) may be obtained by reacting a compound of formula (D)

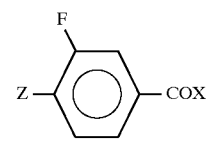

wherein X is hydroxy or halogen (e.g. chlorine) and Z is a group (e.g. NO$_2$) capable of being converted to a nitrogen mustard group M as defined above, with a protected α-amino acid R'-NH$_2$ or oligopeptide R'-NH$_2$ as defined above, followed by conversion of the group Z (e.g. through NH$_2$) to a group M as defined above.

The protected α-amino acids (e.g. t-butylated glutamic acid or aspartic acid) and oligopeptides may be obtained commercially (e.g. from Sigma Chemical Company Limited). Alternatively, they may be prepared by conventional means. For example, glutamic acid may be reacted with t-butylacetate. The compounds of formula (D) may be obtained from 3F, $4NO_2$ toluene which are commercially available (e.g. from Aldrich Chemical Company Limited) by the method of Jackman et al., J. Med. Chem. (1990) 33, 3067–3071 and Marsham et al., ibid 3072–3078.

In a preferred method of producing the compound of formula (C), a compound of formula (E)

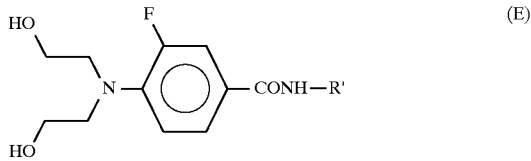
(E)

wherein R'-NH is as defined above, is reacted with a compound of formula

$A-SO_2-B$ wherein A is a methyl or 4-tolyl group, and B is a halogen (e.g. chlorine). The reaction is suitably carried out in an organic solvent, e.g. pyridine.

The compound of formula (E) is preferably prepared by reacting a compound of formula (F)

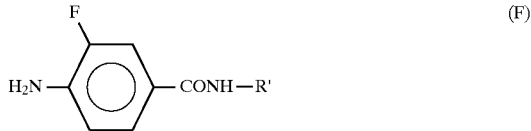
(F)

wherein R'-$NH_2$ is as defined above with ethylene oxide in a solvent, e.g. acetic acid.

The compound of formula (F) is preferably prepared by reducing a compound of formula (G)

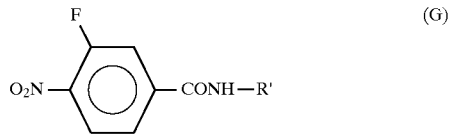
(G)

wherein R'-$NH_2$ is as defined above. The reduction may, for example, be effected by catalytic transfer of the compound of formula (G), e.g. by ammonium formate in methanol in the presence of a Pd/C catalyst.

The compound of formula (G) may be obtained by reacting a compound of formula (D) with an α-amino acid or oligopeptide of formula R'-$NH_2$ as defined above. The reaction is carried out in a solvent such as $CH_2Cl_2$.

The compounds of formulae (A), (C), (E), (F) and (G) may each be purified by conventional means, e.g. chromatography and/or crystallization. These compounds may each be prepared in the form of a salt. Pharmaceutically acceptable salts of the compound of formula (A) include base salts, e.g. those derived from an alkali metal (e.g. sodium) or alkaline earth metal (e.g. magnesium), and ammonium salts; and acid addition salts, including hydrochloride and acetate salts.

The invention includes a pharmaceutical composition comprising a prodrug of the invention and a pharmaceutically acceptable carrier or diluent. The invention also includes a kit comprising a prodrug or composition of the invention and an immunoglobulin/enzyme conjugate in which the immunoglobulin is specific for a tumour-associated antigen and the enzyme will cleave the amide bond between the residue of the α-amino acid R-$NH_2$ or oligopeptide R-$NH_2$ and the benzoic acid nitrogen mustard residue.

The prodrug and immunoglobulin/enzyme conjugate will normally be administered parenterally, e.g. intravenously or intraperitoneally. Thus, the pharmaceutical composition of the invention is normally one which is suitable for parenteral (e.g. intravenous or intraperitoneal) administration. Such a composition conveniently contains the prodrug and isotonic saline or bicarbonate as diluent. The dose of the prodrug and conjugate will ultimately be at the discretion of the physician, who will take into account such factors as the age, weight and condition of the patient. Suitable doses of prodrug and conjugate are given in Bagshawe et al. Antibody, Immunoconjugates, and Radiopharmaceuticals (1991), 4, 915–922. A suitable dose of conjugate may be from 2000 to 200,000 enzyme units/$m^2$ (e.g. 20,000 enzyme units/$m^2$) and a suitable dose of prodrug may be from 20 to 2000 mg/$m^2$ (e.g. 200 mg/$m^2$).

In order to secure maximum concentration of the conjugate at the site of desired treatment, it is normally desirable to space apart administration of the two components by at least 4 hours. The exact regime will be influenced by various factors including the nature of the tumour to be targeted and the nature of the prodrug. A typical regime is to administer the conjugate at 0 h, galactosylated clearing antibody at 24 h, and prodrug at 48 h. If no clearing antibody is used, it would generally be longer than 48 h before the prodrug could be injected.

The following Examples serve to illustrate the invention. The following Reaction Schemes 1 and 2 summarise the processes of Examples 1 and 2 respectively.

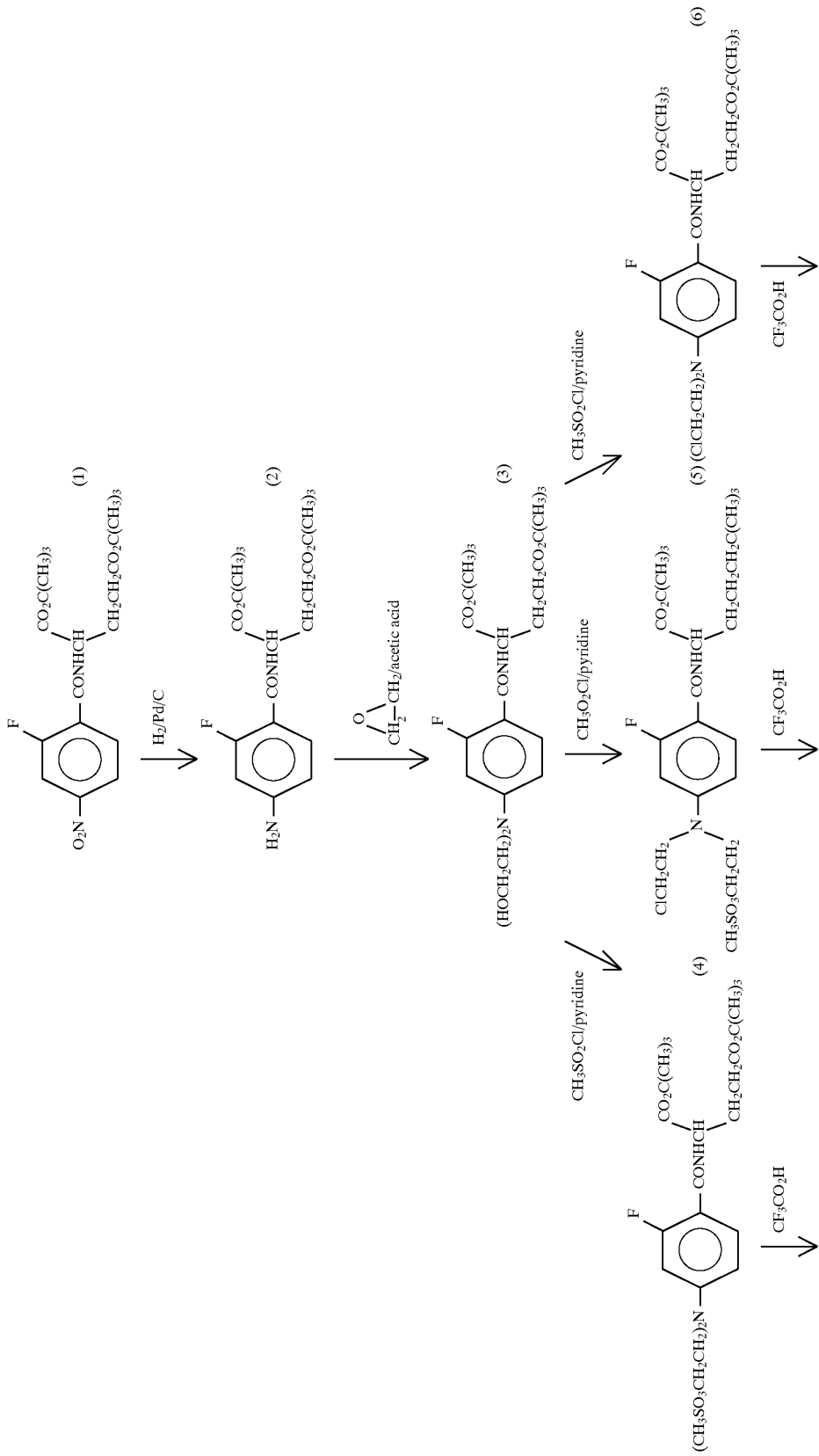

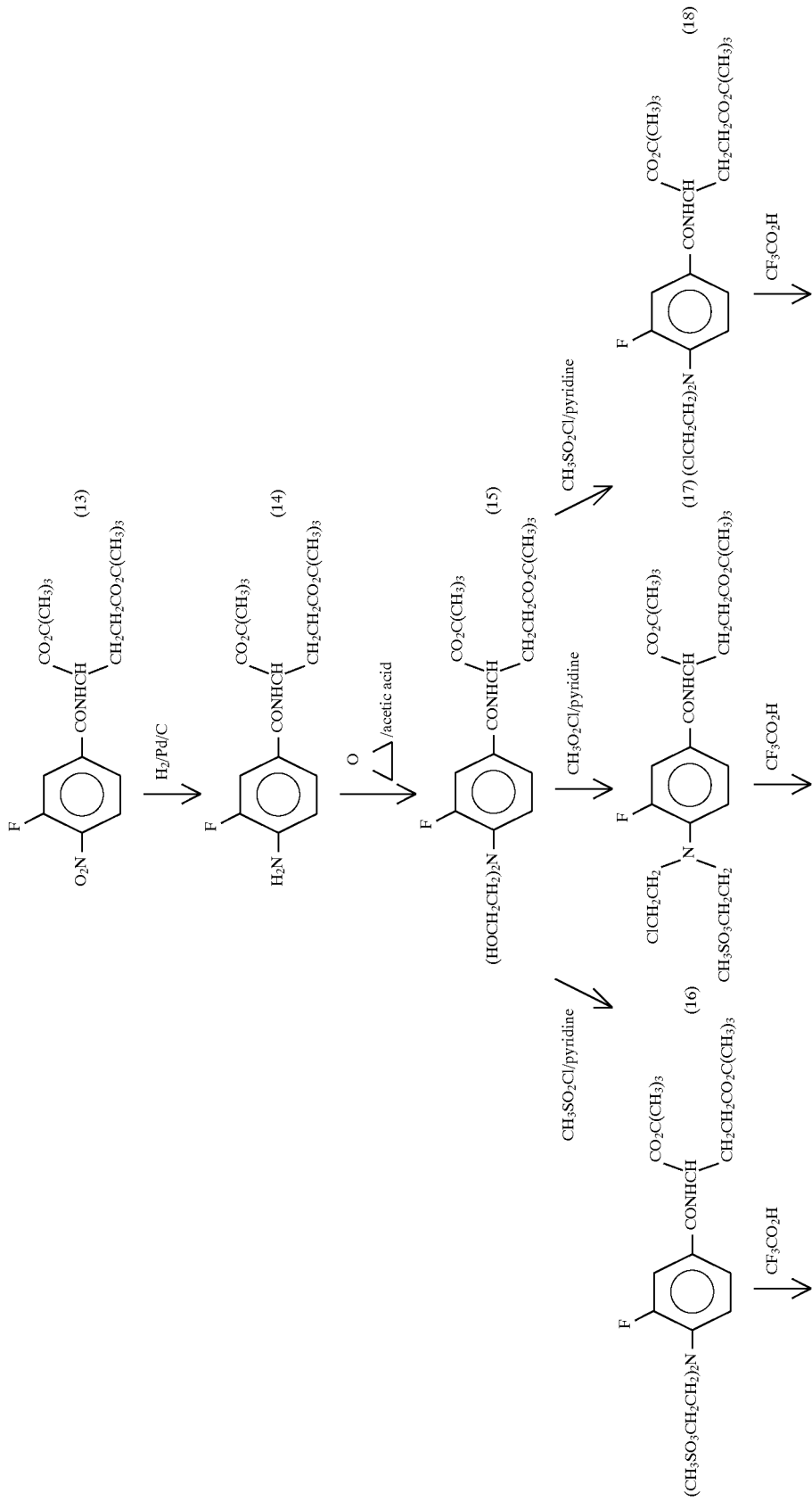

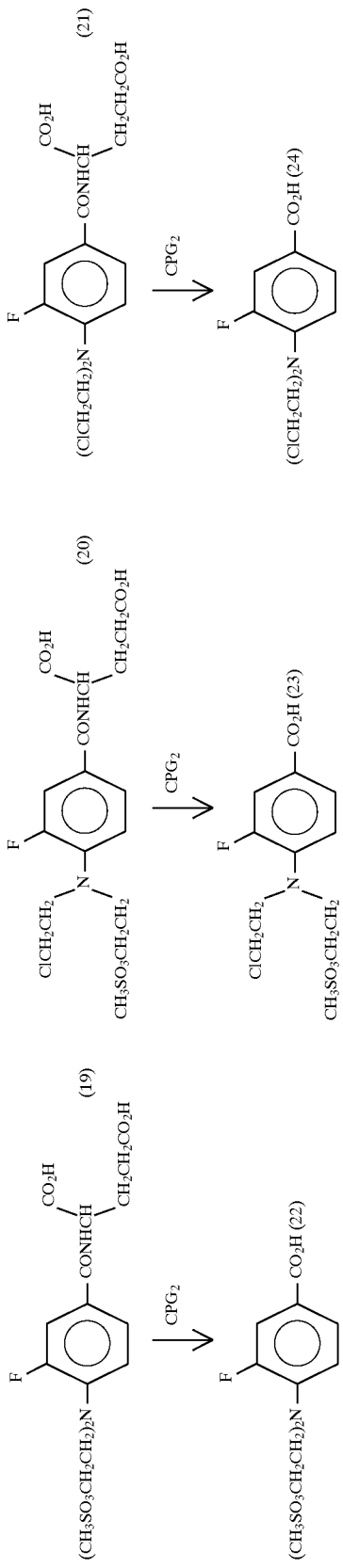

EXAMPLE 1

A Reference Example Showing the Synthesis of 2-Fluoro Prodrugs

Di-tert-butyl 2-fluoro.4-nitrobenzoyl-L-glutamate (1)

To a solution of di-tert butyl L-glutamate hydrochloride (5.0 g, 16.9 mmol) in $Et_3N$ (5.0 ml, 34.0 mmol) was added dropwise a solution of 2-fluoro,4-nitro benzoyl chloride (3.5 g, 17.0 mmol) in $CH_2Cl_2$ (50 ml). Extractive workup gave an oil (1); yield (6.8 g, 94%); $^1H$ NMR ($Me_2SO-d_6$) δ1.40 (s, 9H, t-Bu), 1.43 (s, 9H, t-Bu), 1.95 (m, 2H, C$\underline{H}_2$CH$_2$CO$_2$-t-Bu), 2.34 (t, 2H, J=7.4 Hz, CH$_2$ C$\underline{H}_2$CO$_2$-t-Bu), 4.35 (m,1H, CH), 7.85 (ddd, 1H, $J_{H-6,H-3}$=1.1, $J_{H-6,F}$7.1, $J_{H-6,H-5}$=8.2 Hz H-6), 8.18 (m, 2H, H-3,H-5), 8.92(d, 1H, J=7.46 Hz, NH); $^{19}$NMR ($Me_2SO-d_6$) δ-110.41 (dd, JF,H-$_3$-JF,H$_6$=$^{6.96}$ Hz); mass spectrum (FAB) m/z ([M+H$^+$], 18), 315 (M-t-Bu$_2$, 100); Anal: $C_{20}H_{27}N_2O_7F$-0.04CH$_2$Cl$_2$ requires C-55.99, H-6.35, N-6.52, F-4.42, Cl-0.66, found C-55.64, H-6.08, N-6.41, F-4.44, Cl-0.31. (The presence of $CH_2Cl_2$ noted in the elemental analysis was confirmed by NMR).

Di-tert-butyl 2-fluoro,4-aminobenzovl-L-glutamate (2)

Catalytic transfer reduction of the nitro compound (1) (5.8 g, 13.6 mmol) in MeOH (60 ml) with ammonium formate (4.5 g, 71.5 mmol) over Pd/C (10%) gave the amine (2) as an oil; yield (5.2 g, 96%); $^1$H NMR ($Me_2SO-d_6$) δ1.38 (s, 9H, t-Bu), 1.41 (s, 9H, t-Bu), 1.95 (m, 2H, C$\underline{H}_2$CH$_2$CO$_2$-t-Bu), 2.29 (t, 2H, J=8.13 Hz, CH$_2$CH$_2$CO$_2$-t-Bu), 4.31 (m, 1H, CH), 5.98 (s, 2H, NH$_2$), 6.30 (dd, 1H, JH$_{H-3,F}$=14.33 Hz, H-3), 6.40 (dd, 1H, $J_{H-5,H-6}$=8.57 Hz, H-5), 7.42 (dd, 1H, $J_{H-6,H-6}$=8.70, $J_{H-6,F}$=17.46 Hz, H-6), 7.69 (dd, 1H, $J_{H-N,H-C}$6.75, $J_{H-N,F}$=13.93 Hz, NH); $^{19}$F NMR ($Me_2SO-d_6$) δ-112.23 (ddd); mass spectrum (FAB) m/z (397 [M+H$^+$], 100), 341 (M-t-Bu, 45); Anal: $C_{20}H_{29}N_2O_5F$-0.5MeOH requires C-59.69, H-7.58, N-6.79, F-4.61, found C-59.84, H-7.48, N-7.02, F-4.79.

Di-tert-butyl 2-fluoro,4-[Bis(2-hydroxyethyl)amino]benzoyl-L-glutamate (3)

Amine (2) (1.6 g, 4.0 mmol) in HOAc (10 ml) was stirred with ethylene oxide (13.0 ml, 260 mmol) at room temperature for 112 h. The product was partitioned between $CH_2Cl_2$ and $H_2O$. The organic phase was separated, washed with $H_2O$, dried ($Na_2SO_4$), and evaporated to dryness. The crude oil was chromatographed on silica gel, eluting with EtOAc-$CH_2Cl_2$ to give an oil (3); yield (1.0 g, 49%). $^1$N NMR ($Me_2SO-d_6$) δ1.39 (s, 9H, t-Bu), 1.42 (s, 9H, t-Bu), 1.93 (m, 2H, C$\underline{H}_2$CH$_2$CO$_2$-t-Bu), 2.29 (t, 2H, J=7.69 Hz, CH$_2$ C$\underline{H}_2$CO$_2$-t-Bu), 3.46 (d, 4H, J=5.23 Hz, (HOC$\underline{H}_2$CH$_2$)$_2$), 3.55 (t, 4H, J=4.80 Hz, (HOCH$_2$C$\underline{H}_2$)$_2$), 4.34 (m, 1H, CH), 4.75 (t, 2H, J=4.67 Hz, (OH)$_2$), 6.50 (dd, 1H, $J_{H-3,F}$=17.09 Hz, H-3), 6.57 (dd, 1H, $J_{H-5,H-6}$=8.97 Hz, H-5), 7.33 (dd, 1H, $J_{H-6,F}$=9.1 Hz, H-6), 7.69 (dd, 1H, $J_{H-N,H-C}$=7.11, $J_{H-N,F}$=14.07 Hz, NH); $^{19}$F NMR ($Me_2SO-d_6$) δ-111.03 (ddd); mass spectrum (FAB) m/z (485[M+H$^+$],4), 226 (M-glutBu$_2$, 100); Anal: $C_{24}H_{37}N_2O_7F$-0.5EtOAc requires C-59.07, H-7.82, N-5.30, F-3.59, found C-59.23, H-7.71, N-5.20, F-3.32. (The presence of EtOAc noted in the elemental analysis was confirmed by NMR).

Di-tert-butyl 2-fluoro,4-[Bis(2-(mesyloxy)ethyl)amino]benzoyl-L-glutamate. (4)

Di-tert-butyl 2-fluoro,4-[(2-chloroethyl)[2-(mesyloxy)ethyl)(2-fluoro)amino]benzoyl-L-glutamate (5)

Di-tert-butyl 2-fluoro,4-[Bis(2-chloroethyl)amino]benzoyl-L-glutamate (6)

A solution of (3) (1.4 g, 2.9 mmol) in pyridine (4.5 ml) was stirred with methane sulphonyl chloride (0.9 ml, 1.8 mmol) at 0° C. for 20 min followed by 80° C. for 20 min. The reaction mixture was partitioned between EtOAc and citric acid (10%). The organic phase was separated, washed with $H_2O$, dried ($Na_2SO_4$), and evaporated to dryness. The concentrate contained three reaction products, each of which gave a positive colour with the Epstein reagent. The mixture was chromatographed on silica gel. The slowest eluting was the 2-fluoro, bis[2-(mesyloxy)ethyl-derivative, a solid (4); mp 90°–92° C., yield (0.10 g, 5%); $^1$H NMR ($Me_2SO-d_6$) δ1.38 (s, 9H, t-Bu), 1.42 (s, 9H, t-Bu), 1.94 (m, 2H, C$\underline{H}_2$CH$_2$CO$_2$-t-Bu), 2.30 (t, 2H, J=7.79 Hz, CH$_2$ C$\underline{H}_2$CO$_2$-t-Bu), 3.16 (s, 6H, (C$\underline{H}_3$SO$_3$)$_2$), 3.80 (t, 4H, J=5.21 Hz, (CH$_3$SO$_3$CH$_2$C$\underline{H}_2$)$_2$), 4.33 (t, 5H, J=5.30 Hz, (CH$_3$SO$_3$ C$\underline{H}_2$CH$_2$)$_2$ & CH), 6.68 (dd, 2H, $J_{H-5,H-6}$=8.14, $J_{H-3,F}$=15.27 Hz, H-3, H-5), 7.54 (dd, 1H, $J_{H-6,F}$=9.1 Hz, H-6) 7.90 (dd, 1H, $J_{H-N,H-C}$=5.31, $J_{H-N,F}$=12.52 Hz, NH); $^{19}$F NMR ($Me_2SO-d_6$) δ100.52 (dd); mass spectrum (FAB) m/z (641 [M+H$^+$], 12), 382 (M-glutBu$_2$, 100); Anal: $C_{26}H_{41}N_2O_{11}FS_2$ requires C-48.73, H-6.45, N-4.37, F-2.97, S-10.01, found C-48.62, H-6.26, N-4.32, F-2.73, S-10.09.

Eluting second was an oil, the 2-fluoro, (2-chloroethyl) [2-(mesyloxy)ethyl] derivative (5); yield (0.58 g, 34%); $^1$H NMR ($Me_2SO-d_6$) δ1.38 (s, 9H, t-Bu), 1.42 (s, 9H, t-Bu), 1.93 (m, 2H, C$\underline{H}_2$CH$_2$CO$_2$-t-Bu), 2.30 (t, 2H, J=7.82 Hz, CH$_2$C$\underline{H}_2$CO$_2$-t-Bu), 3.15 (s, 3H, C$\underline{H}_3$SO$_3$), 3.77 (s, 4H, Cl C$\underline{H}_2$CH$_2$), 3.82 (t, 2H, J=5.18 Hz, CH$_3$SO$_3$CH$_2$C$\underline{H}_2$), 4.32 (t, 3H, J=5.17 Hz, CH$_3$SO$_3$C$\underline{H}_2$CH$_2$ & CH), 6.66 (m, 2H, H-3, H-5), 7.55 (dd, 1H, $J_{H-6,H-5}$=8.79, $J_{H-6,F}$=9.2 Hz, H-6), 7.89 (dd, 1H, $J_{H-N,H-C}$=5.64, $J_{H-N,F}$=12.82 Hz, NH); $^{19}$F NMR ($Me_2SO_2-d_6$) δ-110.45 (m); mass spectrum (FAB) m/z (581 [M+M$^+$],14), 322 (M-glutBu$_2$, 100); Anal: $C_{25}H_{38}N_2O_8FClS$ requires C-51.67, H-6.59, N-4.82, F-3.27, Cl-6.10, S-5.52, found C-51.92, H-6.53, N-4.82, F-3.16, Cl-6.06, S-5.48.

The fastest eluting, 2-fluoro, bis(2-chloroethyl) derivative was a solid (6); mp 104°–106° C., yield (0.53 g, 34%); $^1$H NMR ($Me_2SO-d_6$) δ1.38 (s, 9H, t-Bu), 1.42 (s, 9H, t-Bu), 1.96 (m, 2H, C$\underline{H}_2$CH$_2$CO$_2$-t-Bu), 2.29 (t, 2H, J=7.79 Hz, CH$_2$C$\underline{H}_2$CO$_2$-t-Bu), 3.78 (dt, 8H, J=5.29 Hz (Cl C$\underline{H}_2$CH$_2$)$_2$), 4.35 (m, 1H, CH), 6.65 (m, 2H, H-3, H-5), 7.55 (dd, 1H, $J_{H-6\ H-5}$=9.1, $J_{H-6,H-5}$=9.4 Hz, H-6), 7.88 (dd, 1H, $J_{H-N,H-C}$=5.53, $J_{H-N,F}$=12.84 Hz, NH) $^{19}$F NMR ($Me_2SO-d_6$) δ-110.55(ddd,$J_{F,H-N}$=11.26, $J_{F,H-3}$=14.07, $J_{F,H-6}$=16.32 Hz); mass spectrum (FAB) m/z (521 [M+H$^+$], 16), 262 (M-glutBu$_2$, 100) Anal: $C_{24}H_{35}N_2O_5Cl_2$ requires C-55.28, H-6.77, N-5.37, F-3.64, Cl-13.60, found C-55.43, H-6.82, N-5.39, F-3.62, Cl-13.91.

Preparation of diacids-General Method

Compound (4) (0.13 g, 0.20 mmol), (5) (0.21 g, 0.36 mmol), or (6) (0.20 g, 0.38 mmol) was suspended in TFA (4–8% w/v) and stirred for 40 min at room temperature. The solvent was removed under reduced pressure and the remaining oil was diluted with ethyl acetate (1 ml) which was evaporated. This latter step was repeated 5–20 times. Compound (7); yield (0.12 g, 100%), 2-fluoro, 4-[bis-[2-(mesyloxy)ethyl]amino]benzoyl-L-glutamic acid, was obtained as a pure product from (4); $^1$H NMR ($Me_2SO-d_6$) δ2.05 (m, 2H, C$\underline{H}_2$CH$_2$CO$_2$H), 2.32 (t, 2H, J=7.61 Hz, CH$_2$ C$\underline{H}_2$CO$_2$H), 3.16 (s, 6H, (C$\underline{H}_3$SO$_3$)$_2$), 3.81 (t, 4H, J=4.98 Hz, (CH$_3$SO$_3$CH$_2$C$\underline{H}_2$)$_2$), 4.33 (t, 4H, J=5.30 Hz, (CH$_3$SO$_3$ C$\underline{H}_2$CH$_2$)$_2$), 4.41 (t, 1H, J=4.16 Hz, CH), 6.69 (m, 2H, H-3, H-5), 7.58 (dd, 1H, $J_{H-6,F}$=9.1, $J_{H-6,H-5}$=9.3 Hz, H-6), 7.89 (dd, 1H, $J_{H-N,H-C}$=6.04, $J_{H-N,F}$=12.08 Hz, NH); $^{19}$F NMR ($Me_2SO-d_6$) δ-110.35(ddd, $J_{F,H-3}$=14.52 Hz); mass spectrum (FAB) m/z (529[M+H$^+$], 12), 382 (M-glu, 100); Accurate mass Expected 529.0961 found+2.0 ppm; Anal: $C_{18}H_{25}N_2O_{11}FS_2$-0.40TFA-0.30EtOAc requires C-39.99, H-4.67, N-4.67, F-6.96, S-10.68, found C-39.62, H-4.50, N-4.64, F-6.57, S-10.40. (The presence of EtOAc and TFA noted in the elemental analysis was confirmed by NMR). This compound reacted positively with the Epstein spray reagent.

Compound (8); yield (0.17 g, 92%), 2-fluoro, 4-[(2-chloroethyl)[2-(mesyloxy)ethyl]amino]benzoyl-L-glutamic acid, was similarly obtained as an oil from (5); $^1$H NMR (Me$_2$SO-d$_6$) δ2.02 (m, 2H, CH$_2$CH$_2$CO$_2$H), 2.32 (t, 2H, J=7.53 Hz, CH$_2$CH$_2$CO$_2$H) , 3.15 (s, 3H, CH$_3$SO$_3$), 3.77 (s, 4H, ClCH$_2$CH$_2$), 3.82 (t, 2H, J=5.11 Hz, CH$_3$SO$_3$CH$_2$CH$_2$), 4.32, (t, 2H, J=5.31 Hz, CH$_3$SO$_3$CH$_2$CH$_2$), 4.40 (q, 1H, J=4.54 Hz, CH), 6.67 (m, H-3, H-5), 7.57 (dd, 1H, J$_{H-6,F}$=9.1, J$_{H-6,H-5}$=9.4 Hz, H-6), 7.88 (dd, 1H, J$_{H-N,H-C}$=6.53, J$_{H-N,F}$=13.06 Hz, NH); $^{19}$F NMR (Me$_2$SO-d$_6$) δ-110.35 (ddd, J$_{F,H-3}$=16.19 Hz); mass spectrum (FAB) m/z (469 [M+H$^+$),8), 322 (M-glu, 100); Accurate mass Expected 469.0847 found +3.2 ppm; Anal: C$_{17}$H$_{22}$N$_2$O$_8$FClS-0.26TFA-0.15EtOAc requires C-42.52, H-4.62, N-5.48, F-6.60, Cl-6.93, S-6.27, found C-42.12, H-4.68, N-5.13, F-6.20, Cl-6.67, S-6.0. (The presence of EtOAc and TFA, noted in the elemental analysis was confirmed by NMR). This compound reacted positively with the Epstein spray reagent.

Compound (9); yield (0.17 g, 97%), 2-fluoro, 4-[bis(2-chloroethyl)amino]benzoyl-L-glutamic acid, was likewise obtained as an oil from (6); $^1$H NMR (Me$_2$SO-d$_6$) δ1.98 (m, 2H, CH$_2$CH$_2$CO$_2$H), 2.33 (t, 2H, J=7.70 Hz, CH$_2$CH$_2$CO$_2$H), 3.78 (dt, 8H, (ClCH$_2$CH$_2$)$_2$), 4.41 (m, 1H, CH), 6.65 (m, 2H, H-3, H-5), 7.58 (dd, 1H, J$_{H-6,H-5}$=8.83 , J$_{H-6,F}$=9.1 Hz, H-6), 7.85 (dd, 1H, J$_{H-N,H-C}$=5.53, J$_{H-N,F}$=12.84 Hz, NH); $^{19}$F NMR (Me$_2$SO-d$_6$) δ-110.43(ddd, J$_{F,H-3}$=15.27 Hz); mass spectrum (FAB) m/z (409[M+H$^+$]3),262 (M-glu, 100); Accurate mass expected 409.0733 found +3.7 ppm; Anal: C$_{16}$H$_{19}$N$_2$O$_5$FCl$_2$-0.40TFA requires C-44.36, H-4.30, N-6.16, F-9.19, Cl-15.58, found C-44.59, H-4.29, N-5.83, F-8.81, Cl-15.58. (The presence of TFA noted in the elemental analysis was confirmed by NMR). This compound reacted positively with the Epstein spray reagent.

EXAMPLE 2

Synthesis of 3-Fluoro Prodrugs
Di-tert-butyl 3-fluoro,4-nitrobenzoyl-L-glutamate (13)

To a solution of di-tert butyl L-glutamate hydrochloride (20.0 g, 67.6 mol) in Et$_3$N (19 ml, 136.0 mmol) was added dropwise a solution of 3-fluoro,4-nitro benzoyl chloride (13.8 g, 68.0 mmol) in CH$_2$Cl$_2$ (300 ml). Extractive workup gave an oil (13); yield (28.0 g, 97%); $^1$H NMR (Me$_2$SO-d$_6$) δ1.40 (s, 9H, t-Bu), 1.42 (s, 9H, t-Bu), 1.99 (m, 2H, CH$_2$CH$_2$CO$_2$-t-Bu), 2.36 (t, 2H, J=7.45 Hz, CH$_2$CH$_2$CO$_2$-t-Bu), 4.35 (m, 1H, CH), 7.92 (dd, 1H, J$_{H-6,H-5}$=7.56 Hz, H-6), 8.01 (dd, 1H, J$_{H-2,F}$=11.97 Hz, H-2), 8.29 (dd, 1H, J$_{H-5,H-6}$=7.83, J$_{H-5,F}$=16.10 Hz, H-5), 8.97 (d, 1H, J=7.42 Hz, NH); $^9$F NMR (Me$_2$SO-d$_6$) δ-117.98 (dd, J$_{F,H-2}$=7.32, J$_{F,H-5}$=17.8 Hz); mass spectrum (CI) m/z 427 ([M+H$^+$], 100); Anal: C$_{20}$H$_{27}$N$_2$O$_7$F-0.25CH$_2$Cl$_2$ requires C-54.33, H-6.19, N-6.26, F-4.24, Cl-3.96, found C-54.22, H-6.38, N-6.05, F-4.34, Cl-4.15. (The presence of CH$_2$Cl$_2$ noted in the elemental analysis was confirmed by NMR).

Di-tert-butyl 3-fluoro, 4-aminobenzoyl-L-glutamate (14)

Catalytic transfer reduction of the nitro compound (13) (7.5 g, 17.5 mmol) in MeOH (60 ml) with ammonium formate (5.8 g, 91.6 mmol) on Pd/C (10%) gave the amine (14) as an oil (6.9 g, 99%) $^1$H NMR (Me$_2$SO-d$_6$) δ1.39 (s, 9H, t-Bu), 1.40 (s, 9H, t-Bu), 1.97 (m, 2H, CH$_2$CH$_2$CO$_2$-t-Bu), 2.31 (t, 2H, J=7.44 Hz, CH$_2$CH$_2$CO$_2$-t-Bu), 4.28 (m, 1H, CH), 5.71 (s, 2H, NH$_2$), 6.77 (dd, 1H, J$_{H-5,H-6}$=8.77, J$_{H-5,F}$=17.43 Hz, H-5), 7.49 (dd, 1H, J$_{H-6,H-5}$=8.32 Hz, H-6), 7.56 (dd, 1H, J$_{H-2,F}$=12.79 Hz, H-2), 8.19 (d, 1H, J=7.55 Hz, NH); $^{19}$F NMR (Me$_2$SO-d$_6$) δ-135.56 (dd, J$_{F,H-2}$=12.21, J$_{F,H-5}$=20.51 Hz); mass spectrum (FAB) m/z 396 ([M+H$^+$],5} 138 (M-glu, 100); Anal: C$_{20}$H$_{29}$N$_2$O$_5$F requires C-60.59, H-7.37, N-7.07, F-4.79, found C-60.50, H-7.34, N-7.09, F-4.69.

Di-tert-butyl 3-fluoro,4-[Bis(2-hydroxyethyl)amino] benzoyl-L-glutamate (15)

Amine (14) (5.3 g, 13.4 mmol) in HOAc (30 ml) was stirred with ethylene oxide (60 ml, 1.2 mol) at room temperature for 336 h. The solvent was partitioned between EtOAc and H$_2$O. The organic phase was separated, washed with H$_2$O, dried (Na$_2$SO$_4$), and evaporated to dryness. The crude oil was chromatographed on silica gel, eluting with EtOAc-CH$_2$Cl$_2$ to give the pure oil (15); yield (3.3 g, 51%) $^1$H NMR (Me$_2$SO-d$_6$) δ1.39 (s, 9H, t-Bu), 1.41 (s, 9H, t-Bu), 1.97 (m, 2H, CH$_2$CH$_2$CO$_2$-t-Bu), 2.32 (t, 2H, J=7.42 Hz, CH$_2$CH$_2$CO$_2$-t-Bu), 3.43 (t, 4H, J=5.93 Hz, (HOCH$_2$CH$_2$)$_2$), 3.54 (d, 4H, J=5.46 Hz, (HOCH$_2$CH$_2$)$_2$), 4.31 (m, 1H, CH), 4.67 (s, 2H, (OH)$_2$), 6.99, (dd, 1H, J$_{H-5,H-6}$=8.86, J$_{H-5,F}$=17.84 Hz H-5), 7.60 (dd, 2H, J$_{H-6,H-5}$=9.56, J$_{H-2,F}$=14.26 Hz H-6, H-2) 8.30 (d, 1H, J=7.48 Hz, NH); $^{19}$F NMR (Me$_2$SO-d6) δ-124.31 (dd, J$_{F,H-2}$=11.63, J$_{F,H-5}$=17.08 Hz); mass spectrum (FAB) m/z (485 [M+H$^+$], 22), 226 (M-glutBu, 100); Anal: C$_{24}$H$_{37}$N$_2$O$_7$F-1.1EtOAc requires C-58.66, H-7.94, N-4.82, F-3.27, found C-58.31, H-7.83, N-5.18, F-3.49. (The presence of EtOAc noted in the elemental analysis was confirmed by NMR).

Di-tert-butyl 3-fluoro,4-[Bis(2-(mesyloxy)ethyl)amino] benzoyl-L-glutamate (16)
Di-tert-butyl 3-fluoro,4-[(2-chloroethyl) [2-(mesyloxy) ethyl](2-fluoro)amino]benzoyl-L-glutamate (17)
Di-tert-butyl 3-fluoro,4-[Bis(2-chloroethyl)amino]benzoyl-L-glutamate (18)

A solution of (15) (0.67 g, 1.4 mmol) in pyridine (3 ml) was stirred with methane sulphonyl chloride (0.6 ml, 7.7 mmol) at 0° C. for 20 min followed by 80° C. for 15 min. The reaction mixture was partitioned between EtOAc and citric acid (10%). The organic phase was separated, washed with H$_2$O, dried (Na$_2$SO$_4$), and evaporated to dryness. The concentrate contained three reaction products, each of which gave a positive colour reaction with the Epstein reagent. The mixture was chromatographed on silica gel. The slowest eluting oil was the 3-fluoro, bis[2-(mesyloxy)ethyl-derivative, as the oil (16); yield (0.31 g, 35%); $^1$H NMR (Me$_2$SO-d$_6$) δ1.39 (s, 9H, t-Bu), 1.41 (s, 9H, t-Bu), 1.98 (m, 2H, CH$_2$CH$_2$CO$_2$-t-Bu), 2.32 (t, 2H, J=7.42 Hz, CH$_2$CH$_2$CO$_2$-t-Bu), 3.12 (s, 6H, (CH$_2$SO$_3$)$_2$), 3.72 (t, 4H, J=5.41 Hz, CH$_3$SO$_3$CH$_2$CH$_2$)$_2$), 4.30 (t, 5H, J=5.32 Hz, (CH$_3$SO$_3$CH$_2$CH$_2$)$_2$ & CH), 7.16 (dd, 1H, J$_{H-5,H-6}$=8.79, J$_{H-5,F}$=8.8 Hz, H-5) 7.67 (dd, 2H, J$_{H-2,F}$=13.8 Hz, H-2, H-6), 8.43 (d, 1H, J=7.56 Hz, NH); $^{19}$F NMR (Me$_2$SO-d$_6$) δ-122.69 (dd); mass spectrum (FAB) m/z (641 [M+H$^+$], 15), 382 (M-glutBu$_2$, 100); Anal: C$_{26}$H$_{41}$N$_2$O$_{11}$FS$_2$-0.6EtOAc requires C-49.18, H-6.66, N-4.04, F-2.74, S-9.25, found C-48.92, H-6.59, N-4.00, F-2.85, S-8.93. (The presence of EtOAc noted in the elemental analysis was confirmed by NMR).

Eluting second was the 3-fluoro, (2-chloroethyl)[2-(mesyloxy)ethyl] derivative, as the oil (17); yield (0.29 g, 37%); $^1$H NMR (Me$_2$SO-d$_6$) δ1.39 (s, 9H, t-Bu), 1.41 (s, 9H, t-Bu), 1.99 (m, 2H, CH$_2$CH$_2$CO$_2$-t-Bu), 2.32 (t, 2H, J=7.37 Hz, CH$_2$CH$_2$CO$_2$-t-Bu), 3.12 (s, 3H, CH$_3$SO$_3$), 3.71 (s, 6H, ClCH$_2$CH$_2$+CH$_3$SO$_3$CH$_2$CH$_2$), 4.30 (t, 3H, J=5.29 Hz, CH$_3$SO$_3$CH$_2$CH$_2$+CH), 7.13 (dd, 1H, J$_{H-5,H-6}$=8.81, J$_{H-5,F}$=9.0 Hz, H-5), 7.66 (dd, 2H, J$_{H-2,F}$=14.58 Hz, H-2, H-6), 8.41 (d, 1H, J=7.54 Hz, NH); $^{19}$F NMR (Me$_2$SO-d$_6$) δ-123.40 (m); mass spectrum (FAB) m/z (581 [M+H$^+$)30),322

(M-glutBu$_2$, 100); Anal: C$_{25}$H$_{38}$N$_2$O$_8$FClS requires C-51.67, H-6.59, N-4.82, F-3.27, Cl-6.10 S-5.52, found C-51.29, H-6.60, N-4.56, F-3.18, Cl-5.74, S-5.29.

The fastest eluting, 3-fluoro, bis(2-chloroethyl) derivative was the solid (18), mp 100°–103° C.; yield (0.11 g, 15%); $^{19}$H NMR (Me$_2$SO-d$_6$) δ1.39 (s, 9H, t-Bu), 1.41 (s, 9H, t-Bu), 2.01 (m, 2H, CH$_2$CH$_2$CO$_2$-t-Bu), 2.33 (t, 2H, J=7.34 Hz, CH$_2$CH$_2$CO$_2$-t-Bu), 3.72 (s, 8H, (ClCH$_2$CH$_2$)$_2$), 4,32, (m, 1H, CH), 7.11 (dd, 1H, J$_{H-5,H-6}$=8.86, J$_{H-5,F}$=9.1 HZ, H-5), 7.65 (m, 2H, H-2, H-6), 8.40 (d, 1H, J=7.35 Hz, NH); $^{19}$F NMR (Me$_2$SO-d$_6$) δ-123.83 (dd, J$_{F,H-2}$=14.8 Hz); mass spectrum (FAB) m/z (521 (M+H$^+$], 19), 262 (M-glutBu$_2$, 100); Anal: C$_{24}$H$_{35}$N$_2$O$_5$Cl$_2$-0.5H$_2$O requires C-54.34, H-6.84, N-5.28, F-3.58, Cl-13.37, found C-54.71, H-6.61, N-5.31, F-3.64, Cl-13.54.

Preparation of diacids-General method

Compound (16) (0.10 g, 0.16 mmol), (17) (0.08 g, 0.13 mmol), or (18) (0.06 g, 0.11 mmol) was suspended in TFA (4% w/v) and stirred for 40 min at room temperature. The acid was removed under reduced pressure and the remaining oil was diluted with ethyl acetate (1 ml) which was evaporated. This latter step was repeated 5–6 times. Compound (19); yield (0.09 g, 91%) 3-fluoro, 4-[bis-[2-mesyloxy)ethyl]amino]benzoyl-L-glutamic acid, was obtained as a pure product from (16); $^1$H NMR (Me$_2$SO-d$_6$)δ1.99 (m, 2H, CH$_2$CH$_2$CO$_2$H), 2.35 (t, 2H, J=7.45 Hz, CH$_2$CH$_2$CO$_2$H), 3.13 (s, 6H, (CH$_3$SO$_3$)$_2$), 3.72 (t, 4H,J=5.34 Hz, (CH$_3$SO$_3$CH$_2$CH$_2$)$_2$), 4.31 (t, 4H, J=5.16 Hz, (CH$_3$SO$_3$CH$_2$CH$_2$)$_2$), 4.39 (m, 1H, CH), 7.16 (dd, 1H, J$_{H-5,H-6}$=8.59, J$_{H-5,F}$=18.03 Hz, H-5), 7.68 (dd, J$_{H-6,H-5}$=8.91, J$_{H-2,F}$=15.29 Hz, H-2, H-6), 8.45 (d, 1H, J=7.69 Hz, NH); $^{19}$F NMR (Me$_2$SO-d$_6$) δ-122.54(m); mass spectrum (FAB) m/z (529 [M+H$^+$],45) 382 (M-glu, 100); Accurate mass expected 529.0961 found +5.4 ppm; Anal: C$_{18}$H$_{25}$N$_2$O$_{11}$FS$_2$-0.22TFA-0.21EtOAc requires C-40.47, H-4.74, N-4.90, F-5.51, S-11.21, found C-40.87, H-4.76, N-4.75, F-5.85, S-10.98. (The presence of EtOAc and TFA, noted in the elemental analysis was confirmed by NMR). This compound reacted positively with the Epstein spray reagent.

Compound (20); yield (0.06 g, 91%), 3-fluoro, 4-[(2-chloroethyl)[2-(mesyloxy)ethyl]amino]benzoyl-L-glutamic acid, was similarly obtained as an oil from (17); $^1$H NMR (Me$_2$SO-d$_5$) δ2.00 (m, 2H, CH$_2$CH$_2$CO$_2$H), 2.35 (t, 2H, J=7.43 Hz, CH$_2$CH$_2$CO$_2$H), 3.13 (s, 3H, CH$_3$SO$_3$), 3.73 (s, 6H, ClCH$_2$CH$_2$ +CH$_3$SO$_3$CH$_2$CH$_2$), 4.31 (t, 2H, J=5.40 Hz, CH$_3$SO$_3$CH$_2$CH$_2$), 4.39 (m, 1H, CH), 7.15 (dd, 1H, J$_{H-5,H-6}$=8.81, J$_{H-5,F}$=18.24 Hz, H-5), 7.68 (dd, 2H, J$_{H-2,F}$=14.75 Hz, H-2, H-6), 8.45 (d, 1H, J=7.64 Hz, NH); $^{19}$F NMR (Me$_2$SO-d$_6$) δ-123.19 (dd, J$_{F,H-2}$=11.46, J$_{F,H-5}$=14.12 Hz); mass spectrum (FAB) m/z (469 [M+H$^+$], 10), 322 (M-glu, 100); Accurate mass expected 469.0847 found +4.9 ppm; Anal: C$_{17}$H$_{22}$N$_2$O$_8$FClS-0.2OTFA-0.21EtOAc requires C-42.94, H-4.72, N-5.49, F-5.96, Cl-6.95, S-6.28, found C-43.34, H-4.79, N-5.16, F-5.95, Cl-6.82, S-5.89. (The presence of EtOAc and TFA noted in the elemental analysis was confirmed by NMR). This compound reacted positively with the Epstein spray reagent.

Compound (21); yield (0.05 g, 97%), 3-fluoro, 4-[bis(2-chloroethyl),amino] benzoyl-L-glutamic acid, was likewise obtained as an oil from (18): $^1$H NMR (Me$_2$SO-d$_6$) δ2.00 (m, 2H, CH$_2$CH$_2$CO$_2$H), 2.35 (t, 2H, J=7.48 Hz, CH$_2$CH$_2$CO$_2$H), 3.73 (s, 8H, (ClCH$_2$CH$_2$)$_2$), 4.41 (m, 1H, CH), 7.12 (dd, 1H, J$_{H-5,H-6}$=8.78, J$_{H-5,F}$=18.17 Hz, H-5), 7.67 (dd, 2H, J$_{H-2,F}$=15.39 Hz, H-2, H-6), 8.42 (d, 1H, J=7.22 Hz, NH); $^{19}$F NMR (Me$_2$SO-d$_6$) δ-123.65(dd); mass spectrum (FAB) m/z (409 [M+H$^+$],48), 262 (M-glu, 100); Accurate mass expected 409.0733 found -0.7 ppm; Anal: C$_{16}$H$_{19}$N$_2$O$_5$FCl$_2$-0.18TFA-0.2EtOAc requires C-46.07, H-4.68, N-6.26, F-6.54, Cl-15.85, found C-46.29, H-4.80, N-5.99, F-6.29, Cl-15.99. (The presence of EtOAc and TFA noted in the elemental analysis were confirmed by NMR). This compound reacted positively with the Epstein spray reagent.

EXAMPLE 3

Ability of Prodrugs to Act as CPG2 Substrates

The ability of the prodrugs to act as a substrates for CPG2 was tested.

The enzyme kinetics were measured as described in Springer et al., Eur. J. Cancer (1991) 27, 1361–1366. The results are shown in Table 1. All the 3-fluoro substituted prodrugs tested (19, 20 and 21) were found to be good substrates for CPG2. Of the 2-fluoro substituted prodrugs, prodrugs (8) and (9) were good substrates, but prodrug (7) was such a poor substrate that it was not possible to measure its kinetics.

TABLE 1

Kinetics of Prodrugs as substrates for CPG2

| PRODRUG | K$_m$/μmol | k$_{cat}$/S$^{-1}$ |
|---|---|---|
| 7 | very poor substrate | |
| 8 | 11 | 213 |
| 9 | 15 | 462 |
| 19 | 17 | 565 |
| 20 | 6 | 614 |
| 21 | 10 | 1028 |

EXAMPLE 4

Reactivity of the Prodrugs and Active Drugs

The chemical half lives of the prodrugs and the active drugs were measured in order to determine their relative reactivities.

The half lives were measured in a pH stat, by titrating against NaOH, according to Springer et al, Anticancer Drug Design (1991) 6 467–479. The results are shown in Table 2. All three 2-fluoro prodrugs (7, 8, and 9) and their corresponding active drugs (10, 11 and 12) were deactivated. The chemical half lives of the 2-fluoro prodrugs were too long to be measured in a pH stat. In contrast, the 3-fluoro prodrugs (19, 20 and 21) and the corresponding drugs (22, 23 and 24) were activated compared to the corresponding non-fluorinated analogues and 2-fluoro analogues.

TABLE 2

Chemical Half-Lives

| Prodrug | t$_{1/2}$(min) | Active Drug | t$_{1/2}$(min) |
|---|---|---|---|
| 7 | nd | 10 | 93 |
| 8 | nd | 11 | 192 |
| 9 | nd | 12 | 1242 |
| 19 | 9 | 22 | 1.9 |
| 20 | 122 | 23 | 2.4 |
| 21 | 147 | 24 | 72 |
| *25 | 42 | *28 | 21 |
| *26 | 984 | *29 | 58 |
| *27 | 1158 | *30 | 324 |
| nd - not determined | | *For comparison | |

25 = 4-[bis(2-mesyloxy)ethyl]amino]benzoyl-L-glutamic acid

TABLE 2-continued

Chemical Half-Lives

| Prodrug | $t_{1/2}$(min) | Active Drug | $t_{1/2}$(min) |
|---|---|---|---|

26 = 4-[(2-chloroethyl)[2-(mesyloxy)ethyl]amino]benzoyl-L-glutamic acid
27 = 4-[bis(2-chloroethyl)amino]benzoyl-L-glutamic acid
28 = active drug corresponding to 25
29 = active drug corresponding to 26
30 = active drug corresponding to 27

EXAMPLE 5

Cytotoxicity of the Prodrugs With and Without CPG2 in a Colorectal Cell Line The 2- and 3-fluoro prodrugs 7–9 and 19–21, and the non-fluorinated prodrug 26 were tested for prodrug activity by measruing their cytotoxicity with and without CPG2 in the colorectal cell line LS174T for 1 h (Tom et al (1976) In Vitro 12, 180–181). The corresponding active drugs 10–12, 22–24 and 29 respectively were screened under the same conditions.

The results are shown in Table 3. All the 3-fluoro prodrugs 19–21 showed substantial prodrug activity as did the non-fluorinated prodrug 26. In each case the prodrug was completely non-cytotoxic even at 800 $\mu$M and conversion to its corresponding drug by CPG2 led to increased cytotoxicity. The cytotoxicity of each of the active drugs 22–24 and 29 alone was not significantly different from that of its prodrug+CPG2 (19–21 and 26) respectively. Although all the 2-fluoro prodrugs alone were non-toxic, none exhibited prodrug activity since they were not converted to a cytotoxic species in the prodrug+CPG2 tests. These data were in good argument with the cytotoxicity experiments using the 2-fluoro active drugs.

TABLE 3

Biological Assay of the Compounds in Cell Culture with and without CPG2

| Prodrug | IC$_{50}$/$\mu$M | Active Drug | IC$_{50}$/$\mu$M |
|---|---|---|---|
| 7 | >800 | 10 | >800 |
| 7 + CPG2 | >800 | | |
| 8 | >800 | 11 | >800 |
| 8 + CPG2 | >800 | | |
| 9 | >800 | 12 | >800 |
| 9 + CPG2 | >800 | | |
| 19 | >800 | 22 | 480 |
| 19 + CPG2 | 480 | | |
| 20 | >800 | 23 | 280 |
| 20 + CPG2 | 350 | | |
| 21 | >800 | 24 | 270 |
| 21 + CPG2 | 390 | | |
| 26 | >800 | 29 | 185 |
| 26 + CPG2 | 200 | | |

What is claimed is:
1. A compound which is a 3-fluorobenzamide of the formula (A):

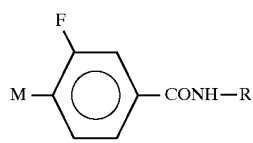

(A)

wherein R-NH is an α-amino acid and —NH is the amino terminal of said α-amino acid, and M is a nitrogen mustard group of the formula

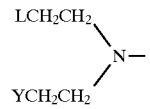

wherein Y and L, which are the same or different in a molecule, and are selected from the group consisting of halo, mesyloxy and 4-tosyloxy; or a pharmaceutically acceptable salt thereof.

2. A compound according to claim 1 wherein Y and L are both mesyloxy, Y and L are both chloro, or Y is mesyloxy and L is chloro.

3. A compound according to claim 1 wherein the amino acid R-NH is glutamic acid or aspartic acid.

4. A compound according to claim 1 wherein the amino acid R-NH is an L-amino acid.

5. A compound which is
   3-fluoro-4-[bis-[2-(mesyloxy)ethyl]amino]benzoyl-L-glutamic acid,
   3-fluoro-4-[(2-chloroethyl) [2-(mesyloxy)ethyl]amino]benzoyl-L-glutamic acid,
   3-fluoro-4-[bis(2-chloroethyl)amino]benzoyl-L-glutamic acid, or a pharmaceutically acceptable salt thereof.

6. A pharmaceutical composition comprising a compound as in claim 1 and a pharmaceutically acceptable carrier or diluent.

7. A compound, according to claim 1 for use in a method of treatment of neoplastic cell growth.

8. A method of treating neoplastic cell growth which comprises administering to a human or animal suffering from neoplastic cell growth, a pharmaceutically effective amount of
   (i) an imunoglobulin/enzyme conjugate in which the immunoglobulin is specific for an antigen associated with said neoplastic cell growth, and the enzyme will cleave the amide bond of the compound of claim 1 between R- and the benzoic acid nitrogen mustard residue; and thereafter
   (ii) a pharmaceutical composition comprising a compound according to claim 1 and a pharmaceutically acceptable carrier or diluent.

9. A process for producing a compound (A) according to claim 1, which process comprises deprotecting a compound of the formula (C)

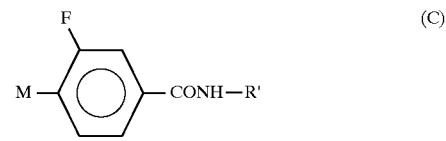

(C)

wherein M is as defined in claim 1, and R'-NH is an α-amino acid containing at least one protected carboxylic acid group, and —NH is the amino terminal of said α-amino acid, and recovering said compound of formula (A).

10. A process according to claim 9 wherein the at least one protected carboxylic acid group is protected by an ethyl or a tertiary butyl group.

11. A process according to claim 12 wherein the compound of formula (C)

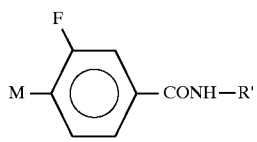

is obtained by reacting a compound of formula (D)

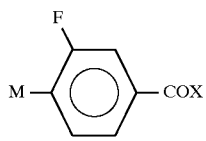

wherein X is hydroxy or halo and Z is a nitro group capable of being converted to a nitrogen mustard group M of the formula

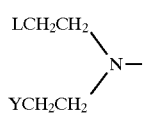

wherein Y and L, which are the same or different in a molecule, and are selected from the group consisting of halo, mesyloxy and 4-tosyloxy, with an α-amino acid containing at least one protected carboxylic acid group, followed by conversion of the group Z to a group M.

12. A method of treating a human or animal patient suffering from neoplastic cell growth, which comprises administering to the patient a pharmaceutically effective amount of a compound according to claim 1, following administration to the patient of an immunoglobulin/enzyme conjugate in which the immunoglobulin is specific for an antigen associated with said neoplastic cell growth and the enzyme is capable of cleaving the amide bond of the compound of claim 1 between R- and the benzoic acid nitrogen mustard residue.

13. The process according to claim 9, including converting said compound of formula (A) into a pharmaceutically acceptable salt thereof.

* * * * *